(12) United States Patent
Luttmann et al.

(10) Patent No.: US 8,846,383 B2
(45) Date of Patent: Sep. 30, 2014

(54) METHOD FOR THE BIOTECHNOLOGICAL PRODUCTION OF VALUABLE PRODUCTS

(75) Inventors: Reiner Luttmann, Braunschweig (DE); Wilfried Kappel, Söhrewald (DE); Toralf Gliem, Melsungen (DE); Mohammad Saeed Ajam, Göttingen (DE); Lars Boettcher, Melsungen (DE); Bernd-Ulrich Wilhelm, Petershagen (DE); Wolfgang Rietschel, Söhrewald (DE)

(73) Assignee: Sartorius AG, Gottingen (DE)

( * ) Notice: Subject to any disclaimer, the term of this patent is extended or adjusted under 35 U.S.C. 154(b) by 1091 days.

(21) Appl. No.: 10/521,387

(22) PCT Filed: Jun. 21, 2003

(86) PCT No.: PCT/EP03/06565
§ 371 (c)(1),
(2), (4) Date: Jan. 14, 2005

(87) PCT Pub. No.: WO2004/018692
PCT Pub. Date: Mar. 4, 2004

(65) Prior Publication Data
US 2006/0014239 A1 Jan. 19, 2006

(30) Foreign Application Priority Data
Aug. 9, 2002 (DE) .................. 102 37 082

(51) Int. Cl.
| C12M 1/12 | (2006.01) |
| B01D 61/14 | (2006.01) |
| B01D 61/22 | (2006.01) |
| C12P 21/00 | (2006.01) |
| C12M 1/00 | (2006.01) |
| C12M 1/34 | (2006.01) |

(52) U.S. Cl.
CPC ............ *B01D 61/147* (2013.01); *B01D 61/142* (2013.01); *B01D 61/145* (2013.01); *B01D 61/22* (2013.01); *C12P 21/00* (2013.01); *C12M 29/04* (2013.01); *C12M 29/18* (2013.01); *C12M 41/36* (2013.01)
USPC .................. 435/297.3; 435/297.2; 435/297.4; 706/7

(58) Field of Classification Search
CPC .. B01D 61/142; B01D 61/145; B01D 61/147; C12P 21/00; C12M 41/36; C12M 29/04; C12M 29/18
USPC .................. 706/7; 435/41, 254.23, 255.5, 938
See application file for complete search history.

(56) References Cited

U.S. PATENT DOCUMENTS

| 4,889,812 | A | * | 12/1989 | Guinn et al. ............... 435/286.7 |
| 5,346,826 | A | * | 9/1994 | Andrews ...................... 435/400 |
| 5,403,479 | A | * | 4/1995 | Smith et al. ............. 210/321.69 |
| 6,168,944 | B1 | * | 1/2001 | Condon et al. ................ 435/239 |
| 6,180,401 | B1 | * | 1/2001 | Chen et al. .................... 435/358 |
| 6,214,574 | B1 | * | 4/2001 | Kopf ............................... 435/41 |
| 6,402,941 | B1 | * | 6/2002 | Lucido et al. .................. 210/94 |
| 6,492,135 | B1 | * | 12/2002 | Larsen ............................ 435/41 |
| 6,599,735 | B1 | * | 7/2003 | Bartok et al. .............. 435/286.5 |
| 6,936,699 | B2 | * | 8/2005 | Peters ........................... 530/412 |
| 2002/0138454 | A1 | * | 9/2002 | Gruenberg et al. .............. 706/7 |
| 2004/0063183 | A1 | * | 4/2004 | Weymarn et al. ............. 435/158 |

FOREIGN PATENT DOCUMENTS

| DE | WO01/85757 A2 * | 11/2001 | ............... C07K 1/00 |
| EP | 0 307 737 A | 3/1989 | |
| WO | WO 91/02049 | 2/1991 | |
| WO | WO 01/32895 | 5/2001 | |

OTHER PUBLICATIONS

G. Cornelissen, H. Leptien, D. Pump, U. Scheffler, E. Sowa, H. H. Radeke and R. Luttmann. "Integrated Bioprocess Development in High Cell Density Cultivation with *Pichia pastoris*." CAB8-Computer Applications in Biotechnology. Jun. 25-27, 2001.*

Nicolas C. Major and Alan T. Bull. "The Physiology of Lactate Production by *Lactobacillus delbreuckii* in a Chemostat with Cell Recycle". Biotechnology and Bioengineering. vol. 34, pp. 592-599 (1989).*

Reiner Luttmann, Gerhard Bitzer, Jens Hartkopf. "Development of control strategies for high cell density cultivations." Mathematics and Computers in Simulation. Elsevier. vol. 37 pp. 153-164 (1994).*

* cited by examiner

*Primary Examiner* — Michael Hobbs
(74) *Attorney, Agent, or Firm* — Gerald E. Hespos; Michael J. Porco; Matthew T. Hespos

(57) ABSTRACT

Disclosed are a method and a device for the biotechnological production of valuable products, in which a medium is fed to a bioreactor and is subjected to a fermentation process, the valuable product is gathered as a filtered permeate and/or concentrated retentate via a cross-flow filtration system that is mounted downstream thereof, and residues are once again fed to the bioreactor until being gathered as a retentate. Other materials can be fed to the bioreactor in a controlled manner in addition to the medium while the concentrated retentate and permeate can be gathered in a controlled manner. The fermentation process and the filtration process are regulated in a synchronized manner in an integrated system via a digital control unit.

14 Claims, 3 Drawing Sheets

METHOD FOR THE BIOTECHNOLOGICAL PRODUCTION OF VALUABLE PRODUCTS

BACKGROUND OF THE INVENTION

The invention relates to a method for biotechnologically producing valuable products, in which method a medium is fed to a bioreactor and subjected to a fermentation process, and in which method the valuable product is harvested, as filtered permeate and/or as concentrated retentate, by way of a downstream cross-flow filtration unit, and residues are supplied again to the bioreactor until harvesting as retentate.

The invention furthermore relates to a device for biotechnologically producing valuable products, which device essentially comprises a bioreactor having an upstream first feed receptacle for a medium and a downstream cross-flow filtration unit whose permeate line is connected to a first harvest receptacle and whose retentate line leads back into the bioreactor.

EP 0 307 737 B1, for example, discloses a method for biotechnically producing valuable products. However, particularly as far as producing recombinant proteins is concerned, a contradiction arises between the requirement for a cell productivity which is as high as possible (high cell density culture) and the requirement for the membranes (cross-flow membranes) of cross-flow microfiltration units to have a long service life. In particular, increasing the permeate flux above a particular limit value at a given biomass concentration in the product solution can lead to a dramatic increase in the transmembrane pressure and, as a result, to the membrane pores becoming blocked, i.e. to the membrane becoming fouled.

BRIEF SUMMARY OF THE INVENTION

The object of the present invention is therefore to improve the fermentation and filtration process so as to make it possible to achieve the aim of the membranes of the cross-flow filtration unit having a service life which is as long as possible at the same time as the cell productivity is as high as possible.

In combination with, a method for biotechnologically producing valuable products in which a medium is fed to a bioreactor and subjected to a fermentation process and in which the valuable product is harvested, as filtered permeate and/or as concentrated retentate, by way of a downstream cross-flow filtration unit, and residues are supplied again to the bioreactor until harvesting as retentate, this object is achieved by it being possible to feed other substances, in addition to the medium, to the bioreactor in a controlled manner, by it being possible to harvest the concentrated retentate and the permeate in a controlled manner, and by the fermentation process and the filtration being regulated, in a manner in which they are matched to each other in an integrated system, by way of a control unit.

By means of the fact that the fermentation process and the filtration are regulated in a manner in which they are matched to each other in an integrated system, such that, in particular, the feeding of substances, and the harvesting can take place in a controlled manner, critical values which could shorten the service life of the membranes are reliably avoided. In particular, it is possible, in this way, to keep the overflow pressure, by which the production solution, which contains the valuable products, is conducted past the membrane, higher than the transmembrane pressure transverse to the membrane, thereby extending the service life of the membrane.

According to a preferred embodiment of the invention, the integrated system can be cleaned and sterilized in situ, with this being controlled by the digital control unit. This thereby makes it possible to achieve rapid and reliable cleaning and sterilization.

According to another preferred embodiment of the invention, recombinant proteins are produced as valuable products, with the permeate yielding a cell-free harvest and the retentate yielding a cell-contaminated harvest. In this connection, the process can proceed while being conducted in a sequential and integrated manner. In this connection, cells which are supplied to the bioreactor can adapt to the medium in a batch phase and the cells can be propagated at a constant growth rate by means of feeding, in a subsequent fed batch phase. The induction of product formation, and the actual production of the recombinant proteins, takes place in a subsequent production phase, by means of adding an inducing substance. In this connection, the concentration of the inducing substance can advantageously be measured by way of flow diffusion analysis and be regulated by feeding from a recipient vessel. A part of the bioreactor is then harvested cell-free in a product harvesting phase which follows the production phase. The cell mass in the retentate is harvested in a cell harvesting phase which can be followed by a medium refreshing phase involving feeding. After the medium refreshing phase, the actual cyclic process, in which, except in the product harvest, only the retentate stream, and not the permeate stream, is to flow, begins once again with the production phase.

According to another preferred embodiment of the invention, the recombinant proteins are produced using the yeast *Pichia pastoris*. While the yeast is easy to culture like *E. coli*, it is, as a eukaryote, much more suitable for achieving correct folding of the recombinant proteins. It is furthermore able to glycolize proteins, something which is important for their structural completeness, their solubility and their biological activity. In addition to this, yeast proteins can be secreted through the cell wall, thereby greatly facilitating the separation of the desired products from cellular constituents.

According to another preferred embodiment of the invention, methanol is added, as inducing substance, to the medium in the bioreactor in order to induce the sequences of the cell protein. The methanol concentration is maintained at a constant level in this connection.

Since the sequences of the target protein are integrated into the native gene segment for expressing a *P. pastoris* alcohol oxidase (AOX), they are induced by adding methanol to the medium.

Overfeeding, which could have a toxic effect, is avoided by keeping the methanol concentration at a level in the lower gram/liter range which is as constant as possible. Maintaining the methanol concentration at a constant level is made possible by measuring the methanol concentration online, and regulating it, by way of the above-mentioned flow diffusion analysis.

According to another preferred embodiment of the invention, glycerol is fed in, in the fed batch phase and/or in the production phase, for increasing production.

According to another preferred embodiment of the invention, the process proceeds while being conducted in a continuous and integrated manner. In this connection, the production phase, the product harvesting phase and the cell harvesting phase proceed in parallel. This makes it possible to achieve permanent product harvesting and turbidostat cell harvesting, with the latter being carried out for the purpose of maintaining satisfactory membrane function.

Since suitable secretory gene sequences are available in the case of *P. pastoris*, the desired products can be produced by means of an integrated bioprocess. In this connection, both process-preparing steps (upstream), beginning with the construction of production-suitable expression systems through to conducting the preculture, and subsequent primary working-up steps (downsteam) can be integrated into the conduct of the actual reaction, i.e. cell culture and product formation. Conducting the process in this way avoids the environmentally damaging working-up steps involved in protein processing when using *E. coli*. In the present case, the product harvest during the course of the culture can be transferred directly to subsequent fine-purification steps for the correctly processed proteins.

The device which is disclosed in EP 0 307 737 B1, for example, suffers from the disadvantages which have been described in the case of the known methods.

Another object of the invention is therefore to improve the known devices such that the known contradiction which exists in connection with producing recombinant proteins, i.e. that of cell productivity being as high as possible while the membranes have a long service life, is resolved.

This object is achieved by a device for biotechnologically producing valuable products, essentially comprising a bioreactor having an upstream first feed receptacle for a medium and a downstream cross-flow filtration unit whose permeate line is connected to a first harvest receptacle and whose retentate line leads back into the bioreactor, by at least one second feed receptacle containing an inducing substance being located upstream of the bioreactor, by a second harvest receptacle for a cell-contaminated harvest of the retentate being connected to the bioreactor by way of a harvest line, and by a control unit being arranged for measuring and regulating the fermentation and filtration process.

The (digital) control unit for measuring and regulating the fermentation and filtration process achieves an optimal process course which enables the membranes to have a long service life in connection with cell productivity being high.

According to a preferred embodiment of the invention, the control unit possesses, for the purpose of measuring the concentration of the inducing substance in the bioreactor, an analytical system which measures the concentration of the inducing substance by way of a sensor which is arranged in the bioreactor and regulates the concentration of inducing substance in the bioreactor by controlling a feed pump which is located upstream of the second feed receptacle. In particular when the process is conducted in a continuous and integrated manner, the analytical system is in the form of a flow diffusion analysis system. This advantageously makes it possible to measure and regulate continuously.

According to another preferred embodiment of the invention, the control unit possesses, for the purpose of measuring a cell concentration in the bioreactor, a second analytical system which measures the cell concentration by way of a second sensor which is arranged in the bioreactor and regulates the cell concentration in the bioreactor by controlling a harvest pump which is located upstream of the second harvest receptacle.

The control unit can undertake all the tasks of a regulatory nature which are typical for a fermentation process, for example measuring and regulating temperature, pH, $pO_2$, by way of gassing rate and gas composition, stirrer speed, foam control, etc. The control unit also undertakes the regulation of the parameters of the automated cross-flow filtration unit, such as permeate flow, retentate flow and the automated in-situ cleaning and sterilization of the integrated system.

Microfiltration and ultrafiltration units, or combinations of microfiltration and ultrafiltration units, are suitable for use as cross-flow filtration units.

BRIEF DESCRIPTION OF THE DRAWINGS

Further details of the invention ensue from the following detailed description and the attached drawings in which preferred embodiments of the invention are illustrated by way of example.

In the drawings.

DETAILED DESCRIPTION OF THE INVENTION

Figure 1:
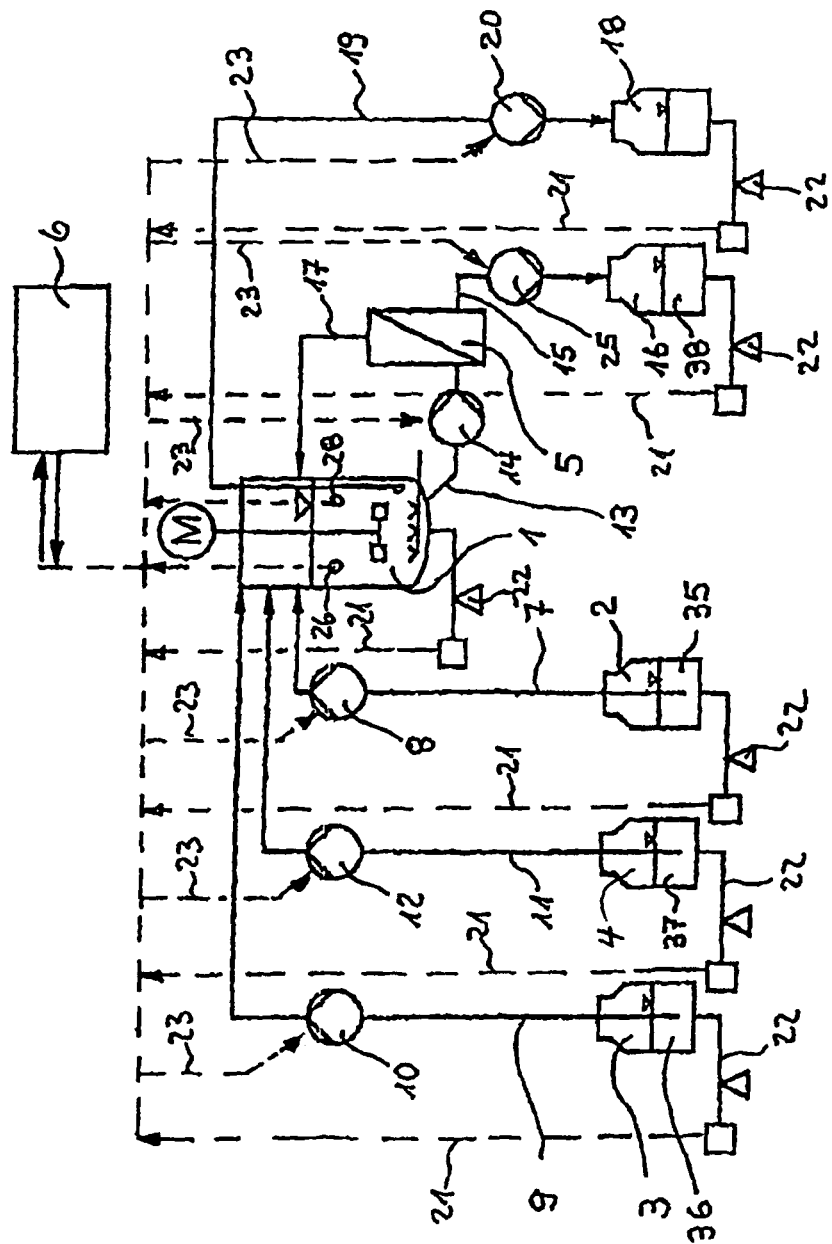
FIG. 1: shows a diagram of a device for biotechnologically producing valuable products.

A device for biotechnologically producing valuable products essentially comprises a bioreactor 1 having an upstream first feed receptacle 2, a second feed receptacle 3, a third feed receptacle 4 and a downstream cross-flow filtration unit 5, and also a control unit 6.

The first feed receptacle 2 is connected to the bioreactor 1 by way of a first feed line 7 and a first feed pump 8. The second feed receptacle 3 is connected to the bioreactor 1 by way of a second feed line 9 and a second feed pump 10. The third feed receptacle 4 is likewise connected to the bioreactor 1 by way of a third feed line 11 and a third feed pump 12.

The cross-flow filtration unit 5 is located downstream of the bioreactor 1 and connected to the bioreactor 1 by way of a conveying line 13. A conveying pump 14 is arranged between the bioreactor 1 and the cross-flow filtration unit 5. The cross-flow filtration unit 5 is connected to a first harvest receptacle 16 by way of a permeate line 15 and a permeate pump 25. The cross-flow filtration unit 5 is connected to the bioreactor 1 by way of a retentate line 17. A second harvest receptacle 18 is connected, for a cell-contaminated harvest of the retentate, to the bioreactor 1 by way of a harvest line 19 and a harvest pump 20.

The digital control unit 6 is connected to weighing devices 22 assigned to the receptacles 2, 3, 4, 16 and 18 by way of measuring lines 21. The control unit 6 is connected to the pumps 8, 10, 12, 14 and 20 by way of control lines 23.

Figure 2:
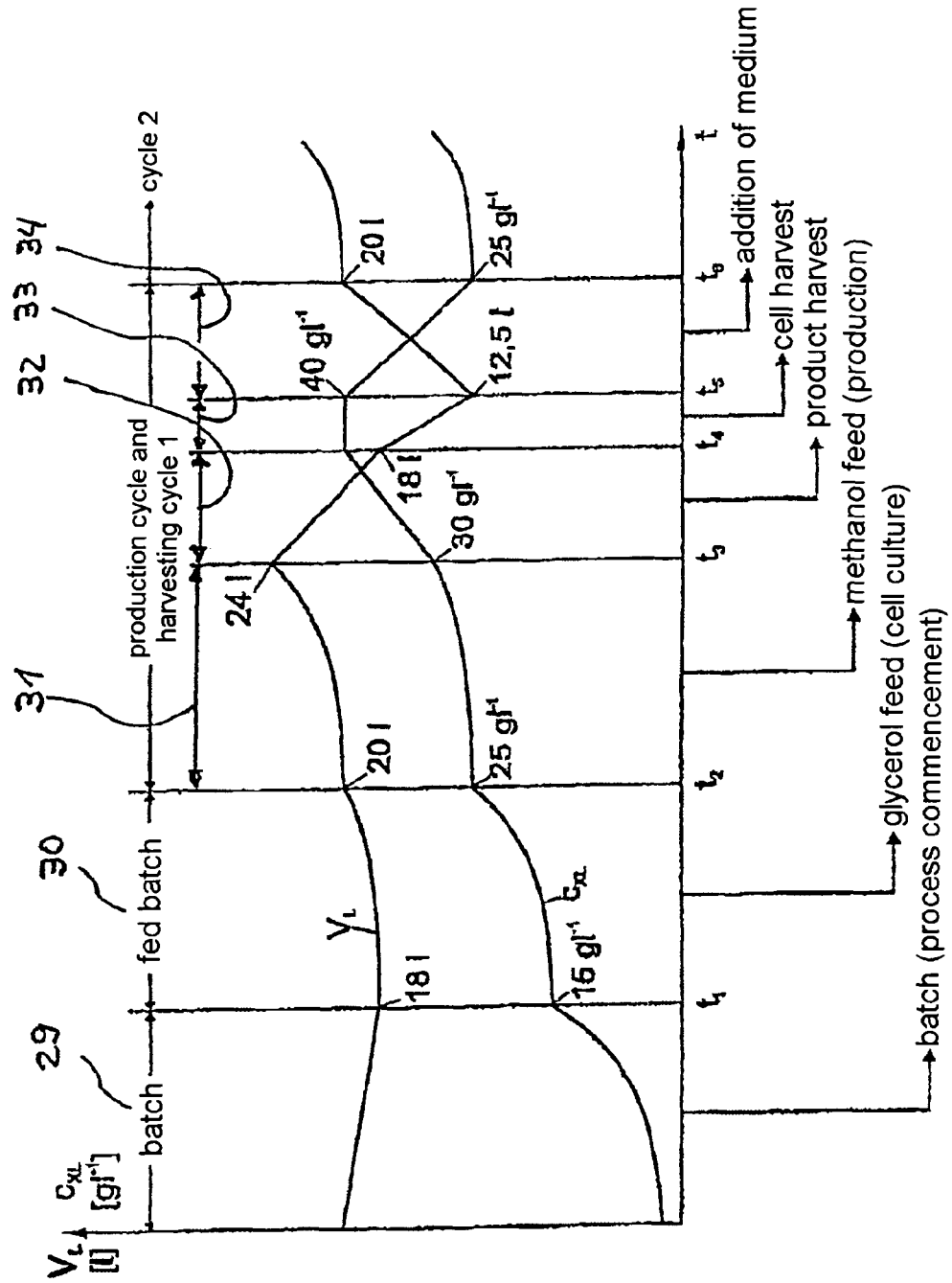
FIG. 2: shows the course of a process which is conducted in a sequentially integrated manner and in which the reactor volume $V_L$ and the cell concentration $c_{x1}$ (dry biomass) are plotted in dependence on the time t.

FIG. 2 depicts the course of a process, which is conducted in a sequentially integrated manner, for producing recombinant proteins using the yeast *P. pastoris*. The reactor volume $V_L$ of the bioreactor 1 and the cell concentration $c_{x1}$ (dry biomass) are plotted. In a batch phase 29 t∈[0, $t_1$], the cells adapt to the medium and are cultured up to approx. 15 gl$^{-1}$. The reactor volume $V_L$ decreases as a result of sample removal.

In a fed batch phase 30 t∈[$t_1$, $t_2$], the cells are grown to 25 gl$^{-1}$, at a constant (substrate-limited) growth rate, by feeding in glycerol 37.

In the production phase 31 t∈[$t_2$, $t_3$], the induction of product formation, and the actual production of the recombinant proteins, first takes place by adding methanol 36 as the inducing substance.

The methanol concentration is measured by an analytical system 24, which belongs to the control unit 6 and is in the form of a flow diffusion analysis (FDA) system, and is regulated, by way of feeding from the second feed receptacle 3, i.e. the methanol recipient vessel, by means of controlling the second feed pump 10.

In order to increase production, a small quantity of glycerol 37 can, in this phase, be added to the bioreactor 1, from the third feed receptacle 4 and by way of the third feed line 11, by means of controlling the third feed pump 12. As a result of adding medium 35 from the first feed receptacle 2 to the bioreactor 1, by way of the first feed line 7, the reactor volume $V_L$ increases and the cells continue to grow at a lower rate (in the example, up to 30 gl$^{-1}$). In the product harvesting phase 32 t$\in$[t$_3$, t$_4$], a quarter (the quantity is optional within limits) of the bioreactor 1 is harvested cell-free as permeate of the cross-flow filtration unit 5. In this connection, the permeate 38 flows, by way of the permeate pump 25 and the permeate line 15, into the first harvest receptacle 16. As a result, the cell concentration increases up to 40 gl$^{-1}$.

From $t_6$ onwards, the procedure starts again with the same production cycle and harvesting cycle as in the case of $t_2$ with approx. 25 gl$^{-1}$. In a cell harvesting phase 33 t$\in$[t$_4$, t$_5$], cell mass or retentate is drawn off from the bioreactor 1 into the second harvest receptacle 18 by way of the harvest pump 20 and the harvest line 19. In a medium refreshing phase 34 t$\in$[t$_5$, t$_6$], methanol-free and glycerol-free medium 35 is added to the bioreactor 1 from the first feed receptacle 2.

The actual cyclic process, in which, except in the product harvest 32, only the retentate stream, and not the permeate stream, is to flow, begins from $t_6$ onwards.

The data for times, percentages, etc., which are specified here are only valid for the process investigated. They can vary greatly. An extension to cell cultures is possible.

When the process is conducted in a continuous and integrated manner, the three phases 31, 32, 33 of the production cycle and harvesting cycle t$\in$[t$_2$, t$_6$] proceed in parallel. This constitutes an interconnected regulation problem which is measured and regulated by way of the digital control unit 6.

Figure 3:
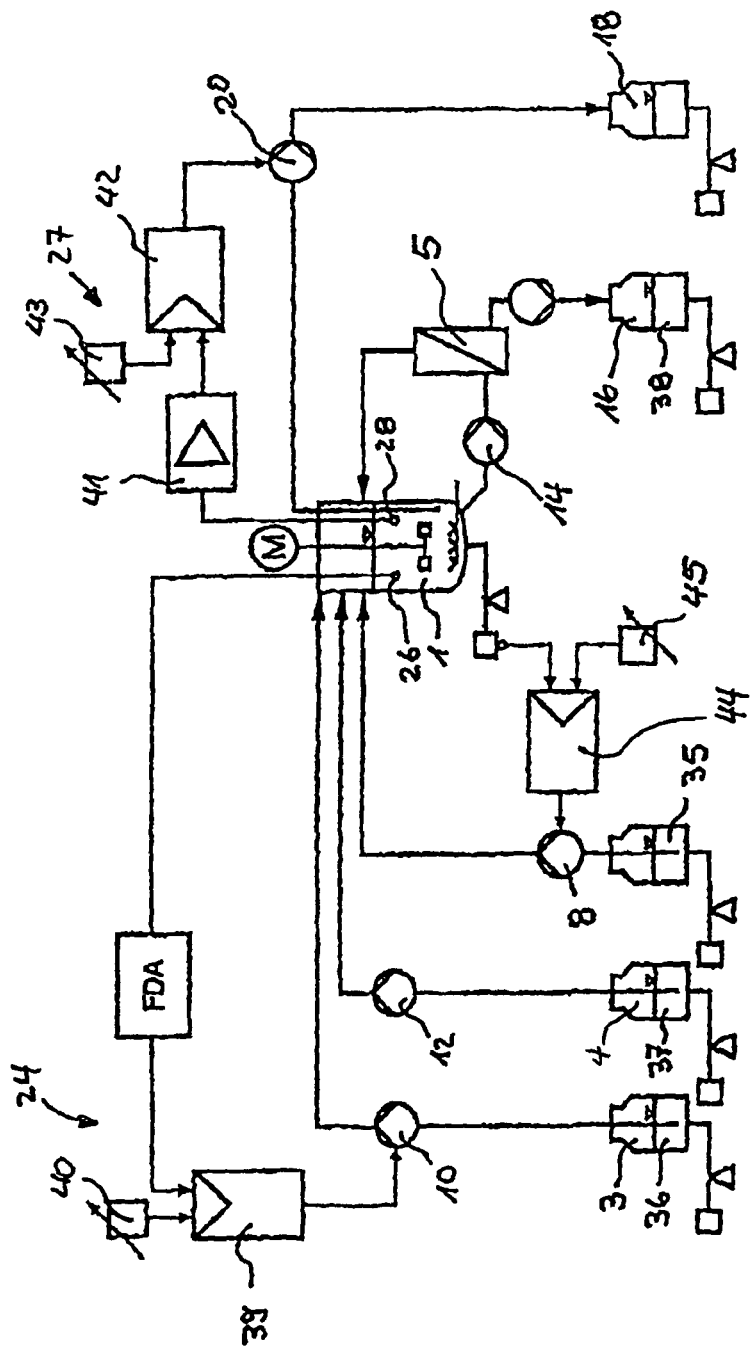
FIG. 3: shows a device for biotechnologically producing valuable products, with the device having a first and second analytical system belonging to a digital control unit which is not further depicted.

FIG. 3 depicts a device for biotechnologically producing valuable products with the process being conducted in a continuous and integrated manner. In this regard, the control unit 6, which is not depicted further in FIG. 3, exhibits an analytical system 24 which measures, by way of a sensor 26 arranged in the bioreactor 1, the concentration of the inducing substance, i.e. the methanol concentration in the example, and regulates the concentration of the inducing substance, or methanol, in the bioreactor 1 by controlling the feed pump 10 which is located upstream of the second feed receptacle 3. In this connection, the analytical system 24 is in the form of a flow diffusion analysis (FDA) system. The flow diffusion analysis is used to measure the actual value of the methanol concentration, which is supplied to a first regulator 39, which compares the actual value with the desired value of a first reference operator 40 and gives a control signal to the second feed pump 10.

In order to measure the cell concentration in the bioreactor 1, the control unit 5 exhibits a second analytical system 27. The second analytical system 27 measures the cell concentration by way of a second sensor 28 which is arranged in the bioreactor 1 and regulates the cell concentration in the bioreactor 1 by controlling a harvest pump 20 which is located upstream of the second harvest receptacle 18. The actual value of the cell concentration is analyzed or measured by way of an analyzer 41 which is connected to the second sensor 28 and supplied to a second regulator 42 which compares the actual value with the desired value of a second reference operator 43 and gives a control signal to the harvest pump 20.

In order to regulate the addition of medium to the bioreactor 1, a third regulator 44 receives an actual signal from the weighing device 22 of the bioreactor 1 and compares the actual signal or the actual value with the desired value of a third reference operator 45 and gives a corresponding control signal to the first feed pump 8.

The invention claimed is:

1. A method for biotechnologically producing valuable products, comprising:
    feeding substances from upstream feed receptacles to a bioreactor by respective feed lines and feed pumps;
    measuring the concentrations of the substances fed into the bioreactor;
    controlling the feed pumps based on the measured concentrations of the substances in the bioreactor;
    subjecting the substances in the bioreactor to a fermentation process;
    conveying product from the bioreactor to a single downstream cross-flow filtration unit to produce a filtered permeate and a rententate;
    conveying the filtered permeate from the cross-flow filtration unit to a first downstream harvest receptacle;
    resupplying said retentate from the cross-flow filtration unit to the bioreactor;
    measuring cell concentration in said bioreactor by a control unit that comprises an analytical system that measures the cell concentration in the bioreactor using a sensor in the bioreactor;
    comparing the measured value of cell concentration with a desired value of cell concentration in a first reference operator;
    regulating the cell concentration in the bioreactor by selectively pumping media from the bioreactor to a second harvest receptacle in response to the comparison of the measured cell concentration in said bioreactor to said desired value of cell concentration;
    measuring the weight of the bioreactor;
    comparing the weight of said bioreactor with a desired weight stored in a second reference operator; and
    based on the comparison of the measured weight and the desired weight, sending a control signal to at least one of the feed pumps, which sends medium to the bioreactor from at least one of said upstream feed receptacles, whereby supplying and harvesting are controlled for improving cell productivity and enhancing service life of the cross-flow filtration unit, wherein the method proceeds while being conducted in a continuous and integrated manner, and wherein in the production phase, the product harvesting phase and the cell harvesting phase proceed in parallel.

2. The method as claimed in claim 1, characterized in that the integrated system can be cleaned and sterilized in situ, with this being controlled by the control unit.

3. The method as claimed in claim 1, characterized in that recombinant proteins are produced as the valuable products, with the permeate yielding a cell-free harvest and the retentate yielding a cell-contaminated harvest.

4. The method as claimed in claim 1, characterized in that the method proceeds while being conducted in a sequential and integrated manner.

5. The method as claimed in claim 3, characterized in that, in a batch phase, cells which are supplied to the bioreactor adapt to the medium and, in a subsequent fed batch phase, the cells are propagated at a constant growth rate by means of feeding.

6. The method as claim in claim 3 characterized in that in a production phase, the induction of product formation, and the actual production of the recombinant proteins, takes place by means of adding an inducing substance.

7. The method as claimed in claim 6, characterized in that the concentration of the inducing substance is measured by way of flow diffusion analysis and regulated by feeding from a second feed receptacle.

8. The method as claimed in claim 4, characterized in that, in a product harvesting phase, a part of the bioreactor is harvested cell-free.

9. The method as claim in claim 8, characterized in that, in a cell harvesting phase, cell mass in the retentate is harvested and this is followed by a medium refreshing phase involving the feeding of the medium.

10. The method as claimed in claim 9, characterized in that, after the medium refreshing phase, the cyclic process, in which, except in the product harvest, only the retentate stream, and not the permeate stream, is to flow, begins once again with the production phase.

11. The method as claimed in claim 3, characterized in that that recombinant proteins are produced using the yeast *Pichia pastoris*.

12. The method as claimed in claim 1, characterized in that methanol is added, as inducing substance, to the medium in the bioreactor in order to induce the sequences of the cell protein.

13. The method as claimed in claim 12, characterized in that the methanol concentration is maintained at a constant level.

14. The method as claimed in claim 11, characterized in that glycerol is fed in, in the fed batch phase and/or in the production phase for increasing production.

* * * * *